(12) United States Patent
Inamdar et al.

(10) Patent No.: US 10,479,769 B2
(45) Date of Patent: Nov. 19, 2019

(54) PROCESSES FOR THE PREPARATION OF ELUXADOLINE

(71) Applicant: SUN PHARMACEUTICAL INDUSTRIES LIMITED, Mumbai, Maharashtra (IN)

(72) Inventors: Murad Ismail Inamdar, Ahmednagar (IN); Sriram Hari Mohan, Krishna (IN); Ketan Vithalbhai Hirpara, Junagadh (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 16/335,013

(22) PCT Filed: Sep. 20, 2017

(86) PCT No.: PCT/IB2017/055704
§ 371 (c)(1),
(2) Date: Mar. 20, 2019

(87) PCT Pub. No.: WO2018/055528
PCT Pub. Date: Mar. 29, 2018

(65) Prior Publication Data
US 2019/0248748 A1    Aug. 15, 2019

(30) Foreign Application Priority Data

Sep. 20, 2016   (IN) .............................. 201611031959

(51) Int. Cl.
*C07D 233/64*    (2006.01)

(52) U.S. Cl.
CPC .................................. *C07D 233/64* (2013.01)

(58) Field of Classification Search
CPC ..................................................... C07D 233/64
USPC ...................................................... 548/340.1
See application file for complete search history.

(56) References Cited

U.S. PATENT DOCUMENTS

| | | |
|---|---|---|
| 5,347,051 A | 9/1994 | Sheehan et al. |
| 7,629,488 B2 | 12/2009 | Cai et al. |
| 7,741,356 B2 | 6/2010 | Breslin et al. |
| 8,710,256 B2 | 4/2014 | Anzalone et al. |
| 2014/0271854 A1 | 9/2014 | Costello et al. |
| 2016/0030393 A1 | 2/2016 | Breslin et al. |

FOREIGN PATENT DOCUMENTS

WO    WO 2009/009480 A3    1/2009

OTHER PUBLICATIONS

International Search Report and Written Opinion for International Application No. PCT/IB2017/055704, issued by US/ISA dated Apr. 26, 2018.
International Preliminary Report on Patentability for International Application No. PCT/IB2017/055704, issued by WIPO, dated 2018.

*Primary Examiner* — Kristin A Vajda

(57) ABSTRACT

The present invention relates to processes for the preparation of eluxadoline. The present invention also provides a compound of Formula V, a process for its preparation, and its use for the preparation of eluxadoline.

10 Claims, No Drawings

PROCESSES FOR THE PREPARATION OF ELUXADOLINE

FIELD OF THE INVENTION

The present invention relates to processes for the preparation of eluxadoline. The present invention also provides a compound of Formula V, a process for its preparation, and its use for the preparation of eluxadoline.

BACKGROUND OF THE INVENTION

Eluxadoline chemically is 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid, represented by Formula I.

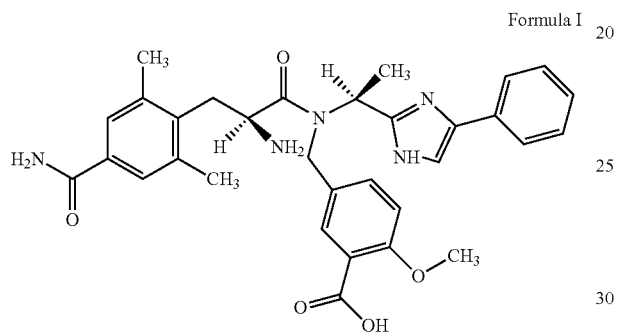

Formula I

Eluxadoline is a mu-opioid receptor agonist, indicated in adults for the treatment of irritable bowel syndrome with diarrhea (IBS-D).

U.S. Pat. No. 7,741,356 describes a process for the preparation of eluxadoline.

U.S. Pat. Nos. 7,629,488 and 8,710,256 describe processes for the preparation of intermediates of eluxadoline.

PCT Publication No. WO2009/009480 allegedly discloses Form a and Form crystals of eluxadoline.

There is a need in the art to develop an improved process for the preparation of eluxadoline.

SUMMARY OF THE INVENTION

The present invention relates to an improved process for the preparation of eluxadoline and its intermediates.

The present invention provides environmentally friendly, cost-effective, easy to handle, and industrially advantageous processes for the preparation of eluxadoline and its intermediates. The processes of the present invention provide eluxadoline having a chromatographic purity of about 97%. The processes of the present invention also provide the compound of Formula V having a chromatographic purity of about 95%.

DETAILED DESCRIPTION OF THE INVENTION

The term "about," as used herein, refers to any value which lies within the range defined by a number up to ±10% of the value.

The term "room temperature," as used herein, refers to a temperature in the range of 25° C. to 35° C.

The term "$C_{1-6}$ alkyl," as used herein, refers to methyl, ethyl, n-propyl, iso-propyl, n-butyl, iso-butyl, sec-butyl, tert-butyl, n-pentyl, neo-pentyl, iso-pentyl, sec-pentyl, n-hexyl, iso-hexyl, 2,3-dimethylbutyl, or neo-hexyl.

The term "nitrogen protecting group," as used herein, refers to benzyloxycarbonyl, acetyl, tert-butoxycarbonyl, trityl, p-toluenesulfonyl, or 9-fluorenylmethoxy carbonyl groups.

A first aspect of the present invention provides a process for the preparation of a compound of Formula V,

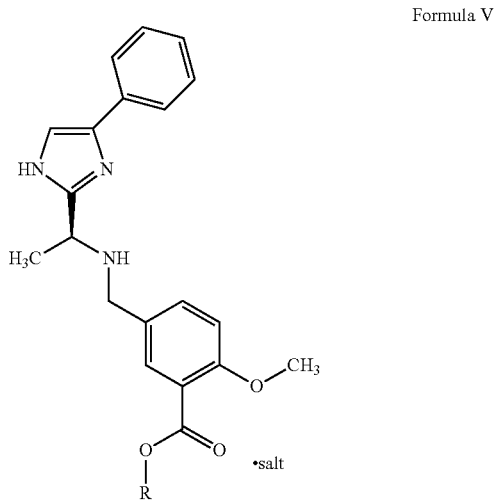

Formula V wherein the salt is selected from the group consisting of citrate, acetate, fumarate, lactate, maleate, malate, tartrate, benzoate, mesylate, oxalate, tosylate, and succinate; and R is hydrogen or $C_{1-6}$ alkyl;

comprising a) deprotecting a compound of Formula II

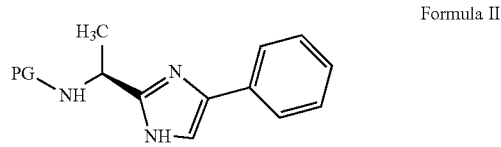

Formula II wherein PG is a nitrogen protecting group;

in the presence of a deprotecting agent to obtain a compound of Formula III; and

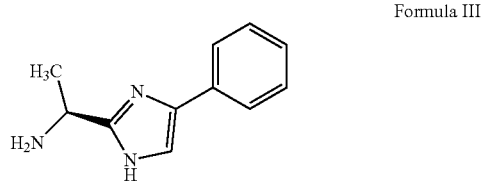

Formula III b) reductive amination of the compound of Formula III with a compound of Formula IV

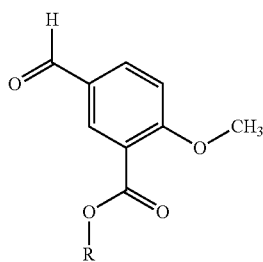

Formula IV wherein R is hydrogen or $C_{1-6}$ alkyl;

followed by the treatment with an acid to obtain a compound of Formula V.

A second aspect of the present invention provides a process for the preparation of eluxadoline of Formula I,

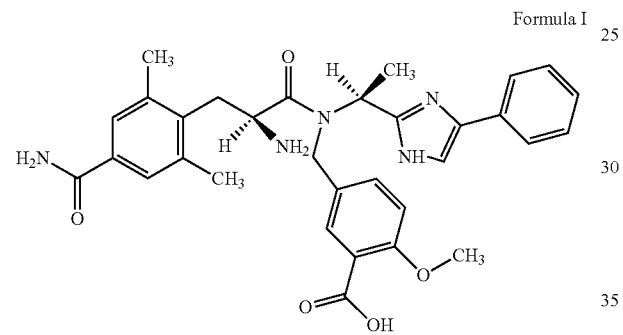

Formula I comprising a) deprotecting a compound of Formula II

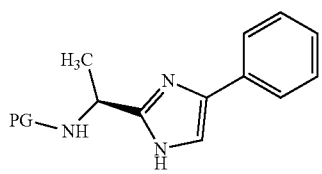

Formula II wherein PG is a nitrogen protecting group;

in the presence of a deprotecting agent to obtain a compound of Formula III;

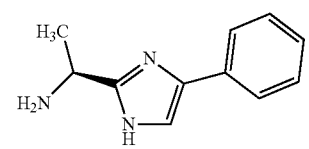

Formula III b) reductive amination of the compound of Formula III with a compound of Formula IV

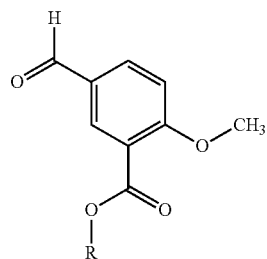

Formula IV wherein R is hydrogen or $C_{1-6}$ alkyl;
followed by the treatment with an acid to obtain a compound of Formula V;

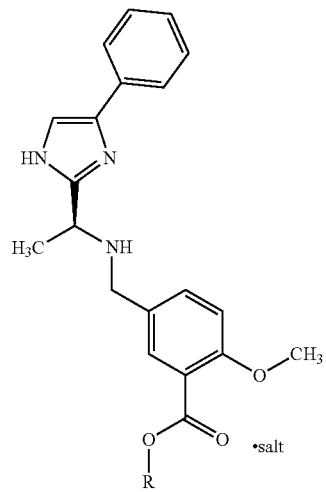

Formula V wherein the salt is selected from the group consisting of citrate, acetate, fumarate, lactate, maleate, malate, tartrate, benzoate, mesylate, oxalate, tosylate, and succinate; and R is hydrogen or $C_{1-6}$ alkyl; and c) converting the compound of Formula V to eluxadoline of Formula I.

A third aspect of the present invention provides a process for the preparation of a compound of Formula V,

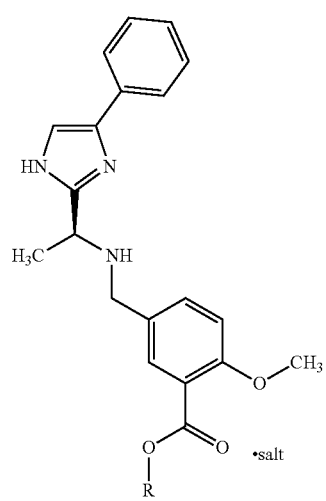

Formula V wherein the salt is selected from the group consisting of citrate, acetate, fumarate, lactate, maleate, malate, tartrate, benzoate, mesylate, oxalate, tosylate, and succinate; and R is hydrogen or $C_{1-6}$ alkyl;

comprising reductive amination of a compound of Formula III

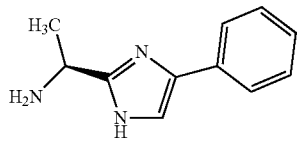

Formula III with a compound of Formula IV

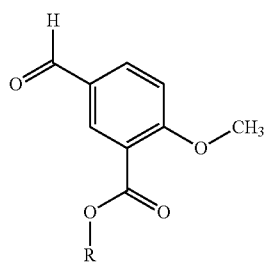

Formula IV wherein R is hydrogen or $C_{1-6}$ alkyl;

followed by the treatment with an acid.

A fourth aspect of the present invention provides a process for the preparation of eluxadoline of Formula I, Formula I comprising a) reductive amination of a compound of Formula III Formula III with a compound of Formula IV

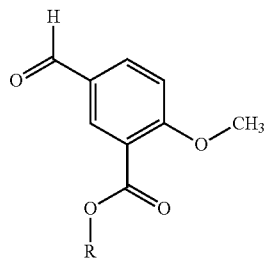

Formula IV wherein R is hydrogen or $C_{1-6}$ alkyl;
followed by the treatment with an acid to obtain a compound of Formula V;

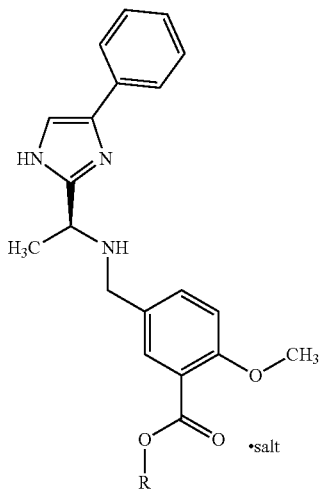

Formula V wherein the salt is selected from the group consisting of citrate, acetate, fumarate, lactate, maleate, malate, tartrate, benzoate, mesylate, oxalate, tosylate, and succinate; and
R is hydrogen or $C_{1-6}$ alkyl; and b) converting the compound of Formula V to eluxadoline of Formula I.

A fifth aspect of the present invention provides a process for the preparation of a compound of Formula Va, Formula Va wherein the salt is selected from the group consisting of citrate, acetate, fumarate, lactate, maleate, malate, tartrate, benzoate, mesylate, oxalate, tosylate, and succinate; comprising a) deprotecting a compound of Formula IIa Formula IIa

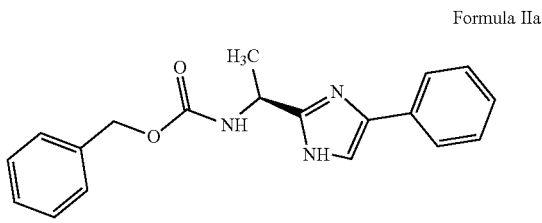 [SMILES: C[C@H](NC(=O)OCc1ccccc1)c1nc(-c2ccccc2)c[nH]1]

in the presence of a deprotecting agent to obtain a compound of Formula III; and Formula II

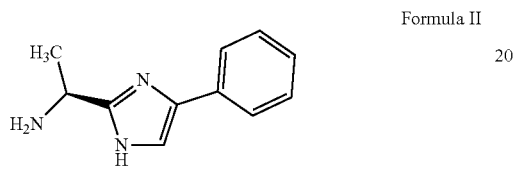

b) reductive amination of the compound of Formula III with a compound of Formula IVa Formula IVa

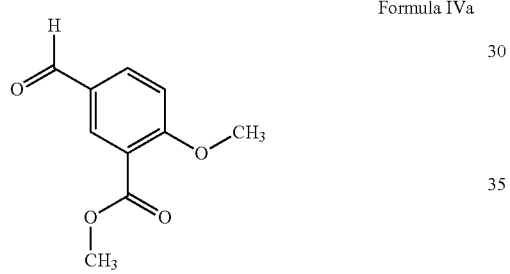

followed by the treatment with an acid.

A sixth aspect of the present invention provides a process for the preparation of eluxadoline of Formula I, Formula I

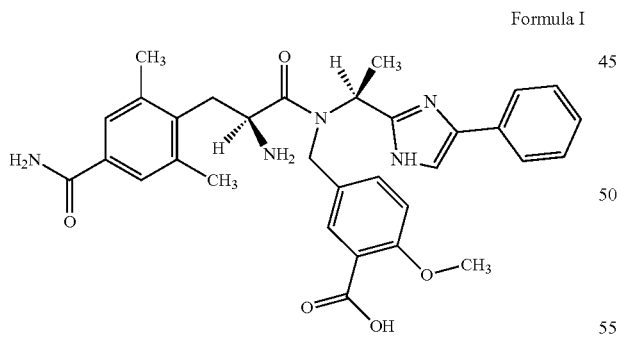

comprising a) deprotecting a compound of Formula IIa

Formula IIa

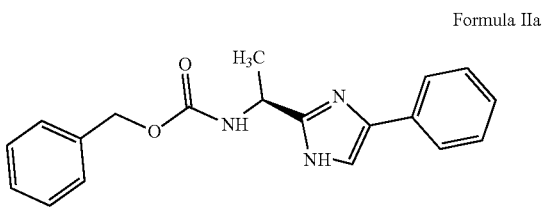 [SMILES: C[C@H](NC(=O)OCc1ccccc1)c1nc(-c2ccccc2)c[nH]1]

in the presence of a deprotecting agent to obtain a compound of Formula III;

Formula III

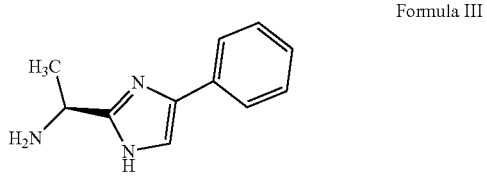

b) reductive amination of the compound of Formula III with a compound of Formula IVa Formula IVa

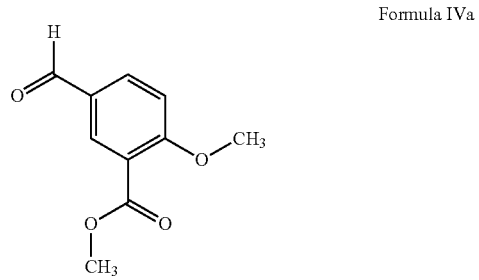

followed by the treatment with an acid to obtain a compound of Formula Va;

Formula Va

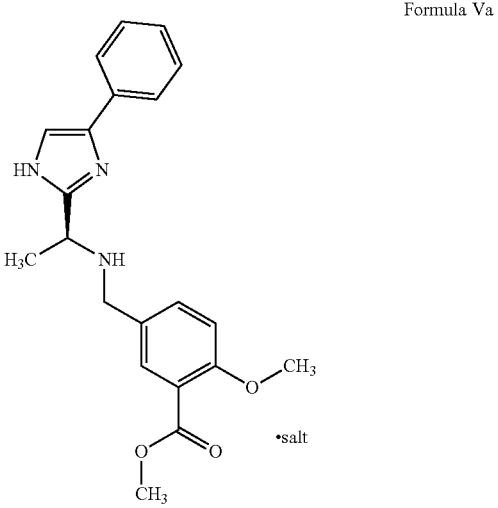 [SMILES: COC(=O)c1cc(CN[C@@H](C)c2nc(-c3ccccc3)c[nH]2)ccc1OC]

wherein the salt is selected from the group consisting of citrate, acetate, fumarate, lactate, maleate, malate, tartrate, benzoate, mesylate, oxalate, tosylate, and succinate; and c) converting the compound of Formula Va to eluxadoline of Formula I.

A seventh aspect of the present invention provides a process for the preparation of a compound of Formula Va, Formula Va

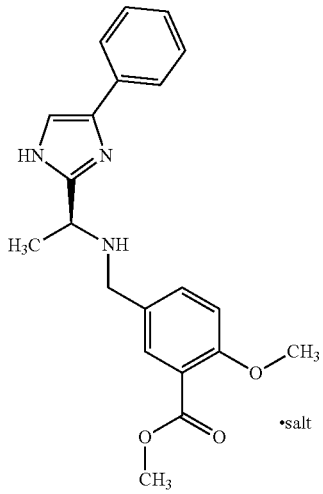

wherein the salt is selected from the group consisting of citrate, acetate, fumarate, lactate, maleate, malate, tartrate, benzoate, mesylate, oxalate, tosylate, and succinate;

comprising reductive amination of a compound of Formula III

Formula III

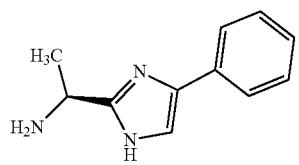

with a compound of Formula IVa

Formula IVa

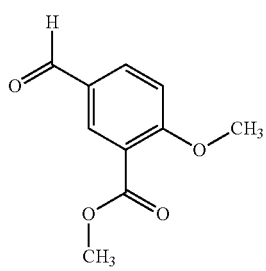

followed by the treatment with an acid.

An eighth aspect of the present invention provides a process for the preparation of eluxadoline of Formula I, Formula I

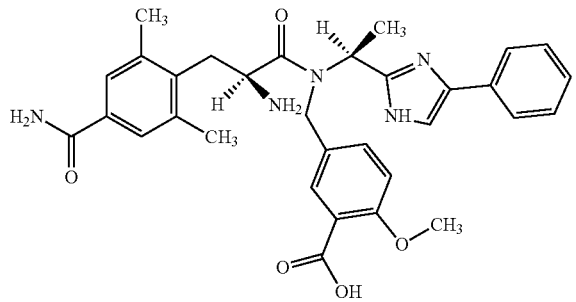

comprising
  a) reductive amination of a compound of Formula III

Formula III

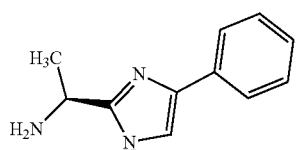

with a compound of Formula IVa

Formula IVa

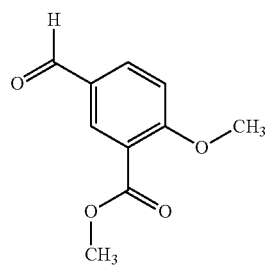

followed by the treatment with an acid to obtain a compound of Formula Va;

Formula Va

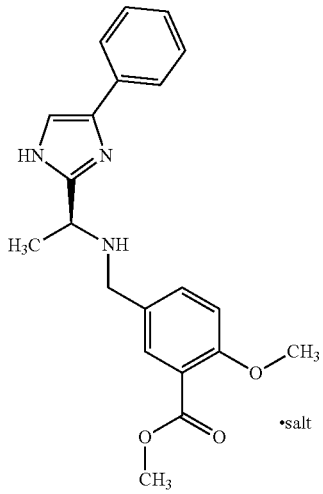

wherein the salt is selected from the group consisting of citrate, acetate, fumarate, lactate, maleate, malate, tartrate, benzoate, mesylate, oxalate, tosylate, and succinate; and
  b) converting the compound of Formula Va to eluxadoline of Formula I.

A ninth aspect of the present invention provides a process for the preparation of eluxadoline of Formula I,

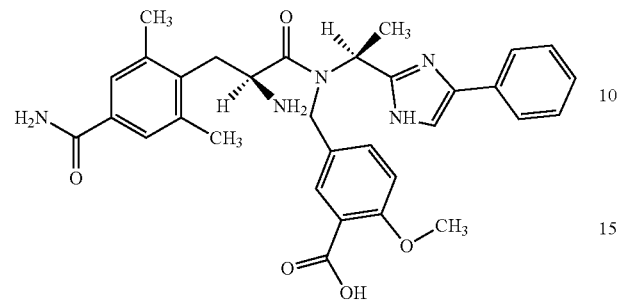

Formula I comprising a) deprotecting a compound of Formula II

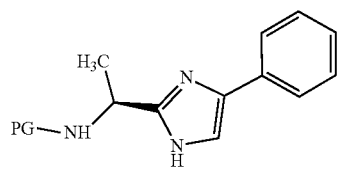

Formula II wherein PG is a nitrogen protecting group;

in the presence of a deprotecting agent to obtain a compound of Formula III;

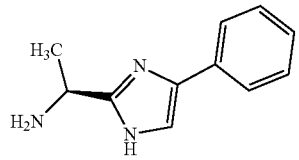

Formula III b) reductive amination of the compound of Formula III with a compound of Formula IV

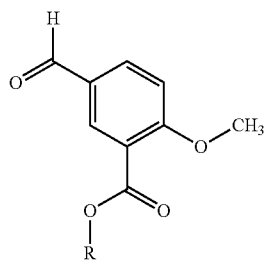

Formula IV wherein R is hydrogen or $C_{1-6}$ alkyl;

followed by the treatment with an acid to obtain the compound of Formula V;

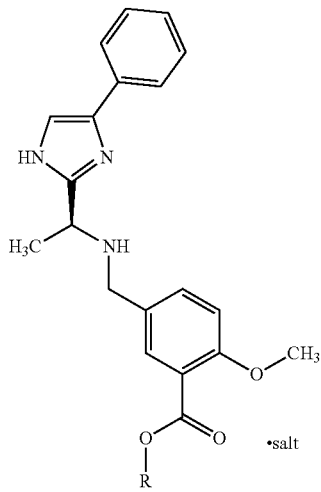

Formula V wherein the salt is selected from the group consisting of citrate, acetate, fumarate, lactate, maleate, malate, tartrate, benzoate, mesylate, oxalate, tosylate, and succinate;

R is hydrogen or $C_{1-6}$ alkyl;

c) treating the compound of Formula V with a base to obtain a compound of Formula VI;

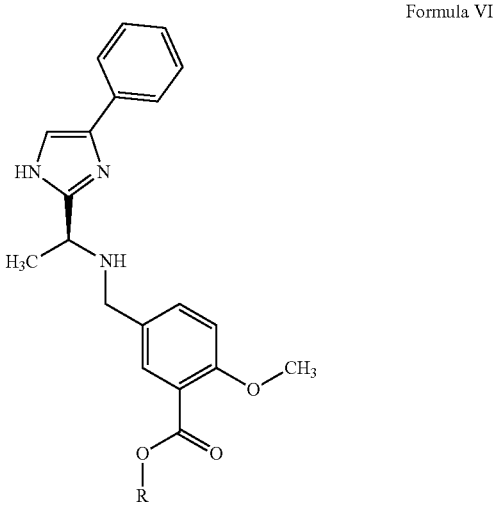

Formula VI wherein R is hydrogen or $C_{1-6}$ alkyl; and d) converting the compound of Formula VI to eluxadoline of Formula I.

A tenth aspect of the present invention provides a process for the preparation of eluxadoline of Formula I,

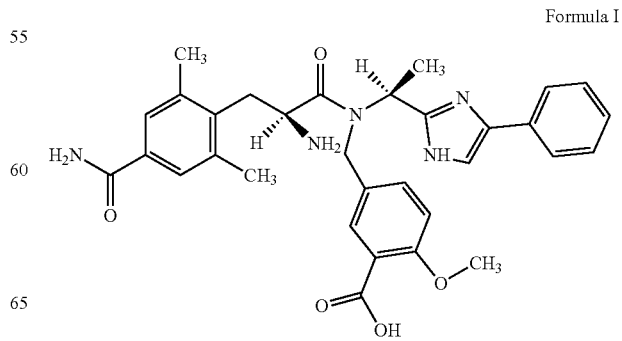

Formula I comprising a) deprotecting a compound of Formula IIa

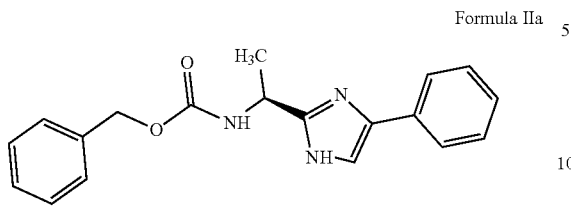

Formula IIa in the presence of a deprotecting agent to obtain a compound of Formula III;

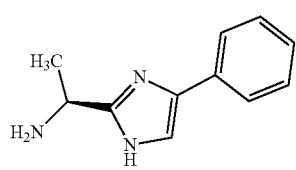

Formula III b) reductive amination of the compound of Formula III with a compound of Formula IVa

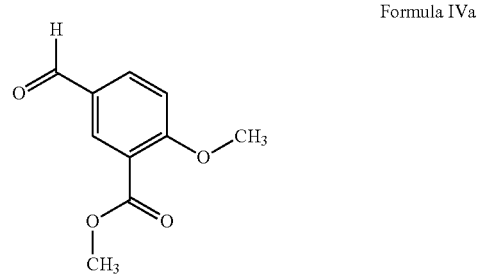

Formula IVa followed by the treatment with an acid to obtain a compound of Formula Va;

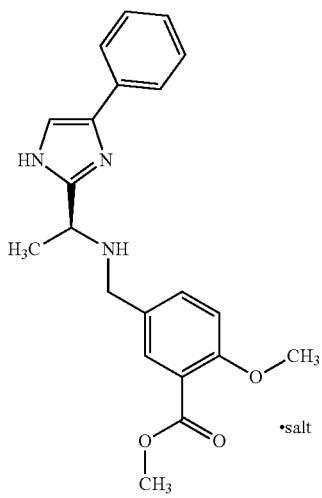

Formula Va wherein the salt is selected from the group consisting of citrate, acetate, fumarate, lactate, maleate, malate, tartrate, benzoate, mesylate, oxalate, tosylate, and succinate;

c) treating the compound of Formula Va with a base to obtain a compound of Formula VIa; and Formula VIa

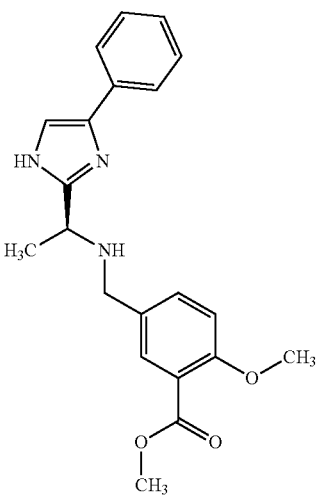

d) converting the compound of Formula VIa to eluxadoline of Formula I.

An eleventh aspect of the present invention provides a process for the preparation of a compound of Formula VI, Formula VI wherein R is hydrogen or $C_{1-6}$ alkyl;

comprising treating a compound of Formula V with a base

Formula V wherein the salt is selected from the group consisting of citrate, acetate, fumarate, lactate, maleate, malate, tartrate, benzoate, mesylate, oxalate, tosylate, and succinate; and R is hydrogen or $C_{1-6}$ alkyl.

A twelfth aspect of the present invention provides a process for the preparation of eluxadoline of Formula I, Formula I

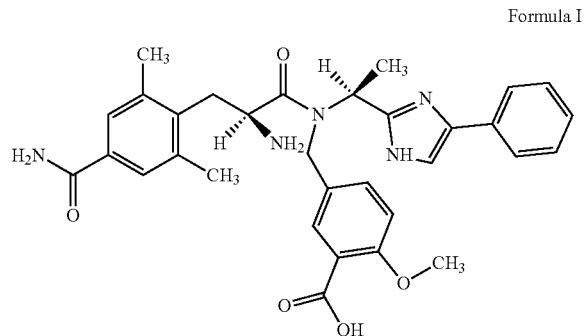 [SMILES: COc1ccc(CN(C(=O)[C@@H](N)Cc2c(C)cc(C(N)=O)cc2C)[C@@H](C)c2nc(-c3ccccc3)c[nH]2)cc1C(=O)O]

comprising
a) treating a compound of Formula V with a base

Formula V

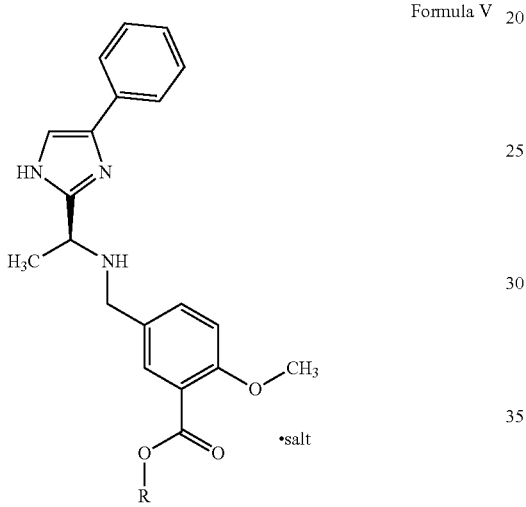

wherein the salt is selected from the group consisting of citrate, acetate, fumarate, lactate, maleate, malate, tartrate, benzoate, mesylate, oxalate, tosylate, and succinate; and
R is hydrogen or $C_{1-6}$ alkyl;
to obtain a compound of Formula VI, Formula VI

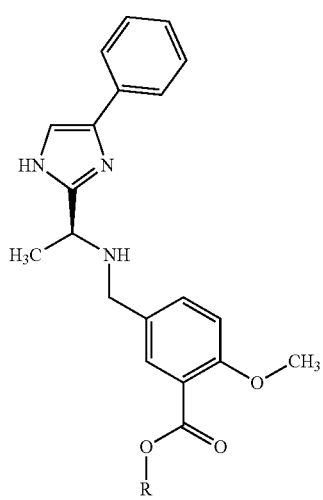

wherein R is hydrogen or $C_{1-6}$ alkyl; and
b) converting the compound of Formula VI to eluxadoline of Formula I.

A thirteenth aspect of the present invention provides a process for the preparation of a compound of Formula VIa, Formula VIa

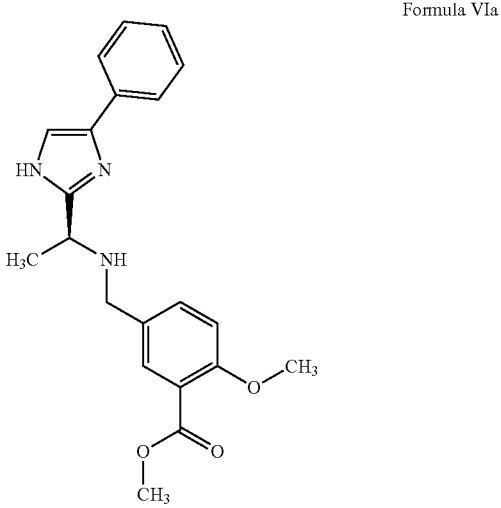 [SMILES: COC(=O)c1cc(CN[C@@H](C)c2nc(-c3ccccc3)c[nH]2)ccc1OC]

comprising treating a compound of Formula Va with a base

Formula Va

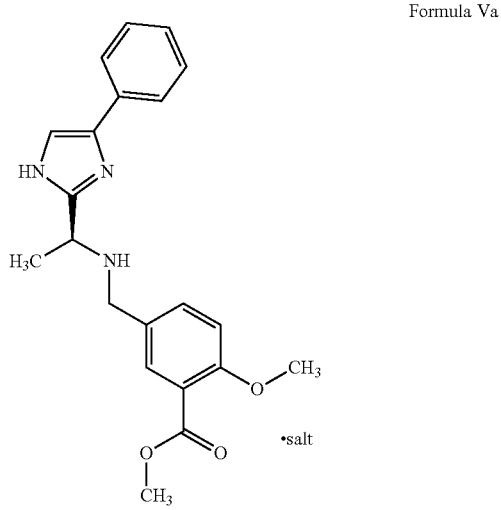 [SMILES: COC(=O)c1cc(CN[C@@H](C)c2nc(-c3ccccc3)c[nH]2)ccc1OC]

wherein the salt is selected from the group consisting of citrate, acetate, fumarate, lactate, maleate, malate, tartrate, benzoate, mesylate, oxalate, tosylate, and succinate.

A fourteenth aspect of the present invention provides a process for the preparation of eluxadoline of Formula I, Formula I

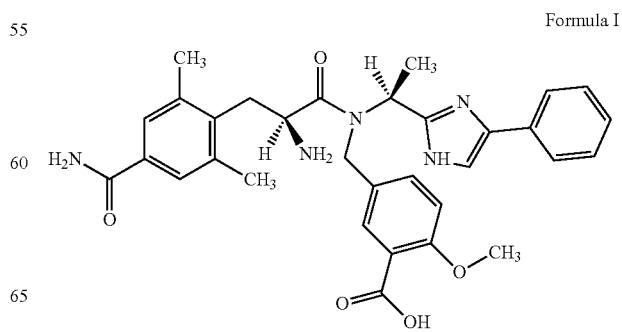

comprising a) treating a compound of Formula Va with a base

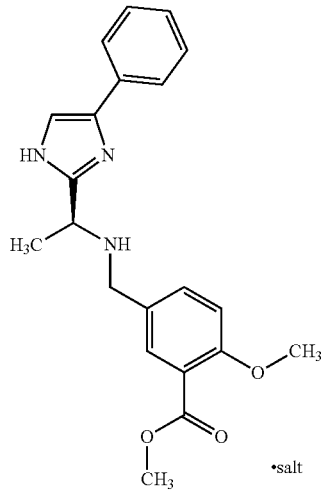

Formula Va

•salt wherein the salt is selected from the group consisting of citrate, acetate, fumarate, lactate, maleate, malate, tartrate, benzoate, mesylate, oxalate, tosylate, and succinate;

to obtain a compound of Formula VIa; and

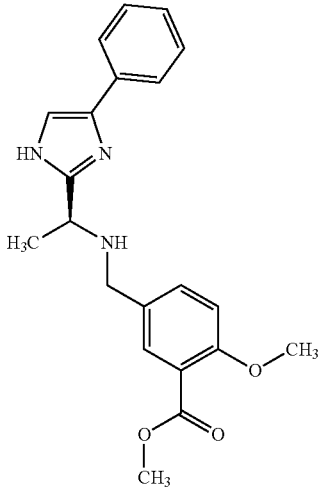

Formula VIa b) converting the compound of Formula VIa to eluxadoline of Formula I.

A fifteenth aspect of the present invention provides a compound of Formula V,

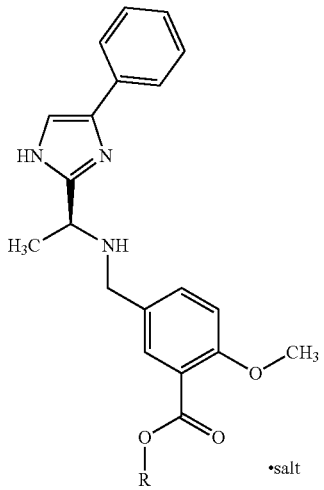

Formula V

•salt wherein the salt is selected from the group consisting of citrate, acetate, fumarate, lactate, maleate, malate, tartrate, benzoate, mesylate, oxalate, tosylate, and succinate; and R is hydrogen or $C_{1-6}$ alkyl.

A sixteenth aspect of the present invention provides use of a compound of Formula V

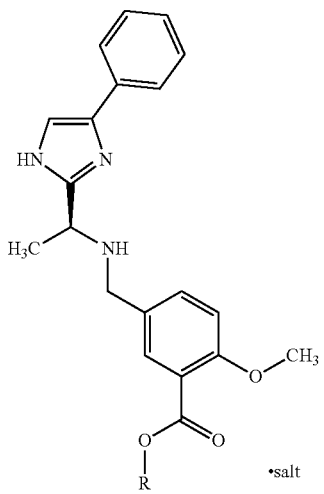

Formula V

•salt wherein the salt is selected from the group consisting of citrate, acetate, fumarate, lactate, maleate, malate, tartrate, benzoate, mesylate, oxalate, tosylate, and succinate; and R is hydrogen or $C_{1-6}$ alkyl;

for the preparation of eluxadoline.

A seventeenth aspect of the present invention provides a compound of Formula Va,

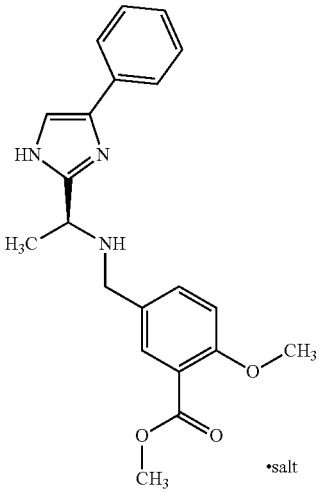

Formula Va wherein the salt is selected from the group consisting of citrate, acetate, fumarate, lactate, maleate, malate, tartrate, benzoate, mesylate, oxalate, tosylate, and succinate.

An eighteenth aspect of the present invention provides use of a compound of Formula Va,

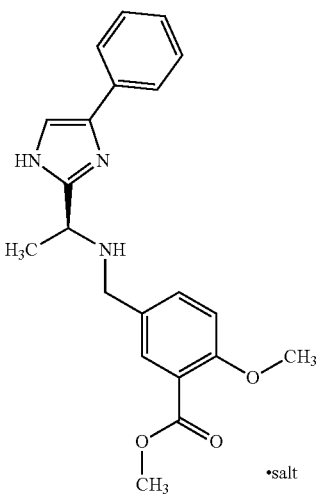

Formula Va wherein the salt is selected from the group consisting of citrate, acetate, fumarate, lactate, maleate, malate, tartrate, benzoate, mesylate, oxalate, tosylate, and succinate; for the preparation of eluxadoline.

The compound of Formula II or IIa may be prepared by any method known in the art, for example, the method described in U.S. Pat. No. 7,741,356.

The deprotection of the compound of Formula II or IIa to obtain the compound of Formula III is carried out in the presence of a deprotecting agent in a solvent.

The deprotecting agent is selected from the group consisting of palladium on carbon (Pd/C), Raney Nickel, and hydrochloric acid.

The deprotection of the compound of Formula II or IIa is carried out under hydrogen pressure of about 3.0 kg/cm$^2$ to about 4.5 kg/cm$^2$.

The solvent is selected from the group consisting of alcohols, nitriles, halogenated hydrocarbons, ethers, water, and mixtures thereof. Examples of alcohols include methanol, ethanol, propanol, iso-propanol, n-butanol, and iso-butanol. An example of nitrile is acetonitrile. Examples of halogenated hydrocarbons include dichloromethane, dichloroethane, chloroform, and carbon tetrachloride. Examples of ethers include tetrahydrofuran, ethyl methyl ether, diethyl ether, and diisopropyl ether.

The deprotection of the compound of Formula II or IIa is carried out in about 30 minutes to about 10 hours, for example, in about 2 hours to about 6 hours.

The deprotection of the compound of Formula II or Formula IIa is carried out at a temperature of about 10° C. to about 40° C., for example, about 20° C. to about 35° C.

The compound of Formula III may optionally be isolated by filtration, decantation, extraction, distillation, evaporation, chromatography, precipitation, concentration, crystallization, centrifugation, and recrystallization. The compound of Formula III may be dried using conventional techniques, for example, drying, drying under vacuum, spray drying, suck drying, air drying, or agitated thin film drying.

The reductive amination of the compound of Formula III with the compound of Formula IV or IVa is carried out optionally in the presence of a reducing agent and molecular sieves in a solvent.

The compound of Formula IV or IVa may be prepared by any method known in the art, for example, the method described in U.S. Pat. No. 7,741,356.

The reductive amination of the compound of Formula III may be carried out after isolation from the reaction mixture in which it is formed, or the reaction mixture containing the compound of Formula III may be used for the reaction with the compound of Formula IV or IVa.

The reducing agent is selected from the group consisting of sodium borohydride, sodium cyanoborohydride, sodium triacetoxyborohydride, lithium borohydride, potassium borohydride, Raney Nickel, and Palladium on carbon (Pd/C).

The reductive amination of the compound of Formula III with the compound of Formula IV or IVa is carried out under hydrogen pressure of about 3.0 kg/cm$^2$ to about 4.5 kg/cm$^2$.

The solvent is selected from the group consisting of alcohols, nitriles, halogenated hydrocarbons, ethers, water, and mixtures thereof. Examples of alcohols include methanol, ethanol, propanol, iso-propanol, n-butanol, and iso-butanol. An example of nitrile is acetonitrile. Examples of halogenated hydrocarbons include dichloromethane, dichloroethane, chloroform, and carbon tetrachloride. Examples of ethers include tetrahydrofuran, ethyl methyl ether, diethyl ether, and diisopropyl ether.

The reaction mixture obtained after the reductive amination of the compound of Formula III with the compound of Formula IV or IVa may be treated with an acid to obtain the compound of Formula V or Va or the reaction mass obtained after the reductive amination of the compound of Formula III with the compound of Formula IV or IVa may be isolated which may further be treated with an acid to obtain the compound of Formula V or Va.

The acid is selected from the group consisting of citric acid, acetic acid, fumaric acid, lactic acid, maleic acid, malic acid, tartaric acid, benzoic acid, methanesulfonic acid, oxalic acid, p-toluenesulfonic acid, and succinic acid.

The reductive amination of the compound of Formula III with the compound of Formula IV or IVa is carried out for about 10 minutes to about 10 hours, for example, for about 10 minutes to about 6 hours.

The reductive amination of the compound of Formula III with the compound of Formula IV or IVa is carried out at a temperature of about 0° C. to about 45° C., for example, about 0° C. to about 30° C.

The treatment of the reaction mixture with an acid is carried out for about 1 hour to about 30 hours, for example, for about 1 hour to about 24 hours.

The treatment of the reaction mixture with an acid is carried out at a temperature of about 5° C. to about 60° C., for example, about 10° C. to about 55° C.

The compound of Formula V or Va may optionally be isolated by filtration, decantation, extraction, distillation, evaporation, chromatography, precipitation, concentration, crystallization, centrifugation, and recrystallization. The compound of Formula V or Va may be dried using conventional techniques, for example, drying, drying under vacuum, spray drying, air drying, or agitated thin film drying.

The treatment of the compound of Formula V or Va with a base to obtain the compound of Formula VI or VIa is carried out in a solvent.

The base is selected from the group consisting of sodium hydroxide, potassium hydroxide, lithium hydroxide, calcium hydroxide, sodium bicarbonate, potassium bicarbonate, and cesium hydroxide.

The solvent is selected from the group consisting of alcohols, nitriles, halogenated hydrocarbons, ethers, water, and mixtures thereof. Examples of alcohols include methanol, ethanol, propanol, iso-propanol, n-butanol, and iso-butanol. An example of nitrile is acetonitrile. Examples of halogenated hydrocarbons include dichloromethane, dichloroethane, chloroform, and carbon tetrachloride. Examples of ethers include tetrahydrofuran, ethyl methyl ether, diethyl ether, and diisopropyl ether.

The treatment of the compound of Formula V or Va with a base is carried out for about 5 minutes to about 10 hours, for example, for about 10 minutes to about 4 hours.

The treatment of the compound of Formula V or Va with a base is carried out at a temperature of about 15° C. to about 40° C., for example, about 18° C. to about 25° C.

The reaction mixture containing the compound of Formula VI or VIa may be used as such for the preparation of eluxadoline or the compound of Formula VI or VIa may optionally be isolated by filtration, decantation, extraction, distillation, evaporation, chromatography, precipitation, concentration, crystallization, centrifugation, and recrystallization. The compound of Formula VI or VIa may be dried using conventional techniques, for example, drying, drying under vacuum, spray drying, air drying, or agitated thin film drying.

The compound of Formula VI or VIa is converted to methyl 5-({[N-(tert-butoxycarbonyl)-4-carbamoyl-2,6-dimethyl-L-phenylalanyl][(1S)-1-(4-phenyl-1H-imidazol-2-yl)ethyl]amino}methyl)-2-methoxybenzoate by following the process known in the art, for example, as disclosed in U.S. Pat. No. 7,741,356 or as described herein.

Methyl 5-({[N-(tert-butoxycarbonyl)-4-carbamoyl-2,6-dimethyl-L-phenylalanyl][(1S)-1-(4-phenyl-1H-imidazol-2-yl)ethyl]amino}methyl)-2-methoxybenzoate is converted to eluxadoline of Formula I by the processes known in the art, for example, as disclosed in U.S. Pat. No. 7,741,356 or as described in our copending application.

While the present invention has been described in terms of its specific aspects and embodiments, certain modifications and equivalents will be apparent to those skilled in the art, and are intended to be included within the scope of the present invention.

Method

Chromatographic purity of the samples was determined by HPLC using Water® Alliance® HPLC system, Water 2695 separation module with 2489 UV visible detector.

The NMR spectrum was recorded using a Bruker® Avance III (400 MHz) NMR spectrometer.

The IR spectrum was recorded using a Perkin Elmer® instrument.

The Mass spectrum was recorded using a MASS (API2000) LC/MS-MS system, Q Trap® LC/MS-MS system (Applied Biosystems).

The following examples are for illustrative purposes only and should not be construed as limiting the scope of the invention in any way.

EXAMPLES

Reference Example

Preparation of methyl 2-methoxy-5-({[(1S)-1-(4-phenyl-1H-imidazol-2-yl)ethyl]amino}methyl)benzoate (Formula VI) as per procedure disclosed in U.S. Pat. No. 7,741,356

Benzyl [(1S)-1-(4-phenyl-1H-imidazol-2-yl)ethyl]carbamate (25 g; Formula IIa or Formula II, when PG is benzyloxycarbonyl) was added to methanol (125 mL) at room temperature to obtain a mixture. Palladium on carbon (Pd/C) (2.5%; 50% wet; 3.75 g) was added to the mixture at room temperature. Hydrogen pressure (3 $kg/cm^2$ to 4 $kg/cm^2$) was applied to the reaction mass and then stirred for 4 hours at room temperature. The reaction mixture was filtered through Hyflo® bed and then washed with methanol (50 mL) to obtain a filtrate.

Methyl 5-formyl-2-methoxybenzoate (16.54 g; Formula IVa or IV, when R is methyl) was added to the filtrate at room temperature to obtain a reaction mixture. The reaction mixture was stirred for one hour at room temperature and then cooled to 0° C. Sodium borohydride (4.39 g) was added in lots to the reaction mixture and then stirred for 4 hours at 0° C. to 10° C. Sodium borohydride (1.1 g) was again added in lots at 0° C. to 10° C. and then stirred for 2 hours at 0° C. to 10° C. Water (75 mL) and dichloromethane (105 mL) were added to the reaction mixture at 0° C. to 10° C. and then stirred for 10 minutes. The layers were separated and the organic layer was washed with 5% sodium bicarbonate (75 mL) at 0° C. to 10° C. The aqueous layer was extracted with dichloromethane (45 mL) at 0° C. to 10° C. The combined organic layers were recovered under vacuum at 45° C. to obtain the title compound.

Yield: 28.22 g

Chromatographic purity: 74.1%

Example 1: Preparation of methyl 2-methoxy-5-({[(1S)-1-(4-phenyl-1H-imidazol-2-yl)ethyl]amino}methyl)benzoate citrate (Formula Va or V, when R is methyl)

Method A:

Methanol (1.2 L) and benzyl [(1S)-1-(4-phenyl-1H-imidazol-2-yl)ethyl]carbamate (300 g; Formula IIa or Formula II, when PG is benzyloxycarbonyl) were added into the hydrogenation vessel at room temperature. Palladium on carbon (Pd/C) (2.5%, 50% wet; 45 g) was added to the vessel at room temperature. Nitrogen (1 $kg/cm^2$) was applied and the operation was repeated and then hydrogen pressure (3.5 $kg/cm^2$ to 4 $kg/cm^2$) was applied. The reaction mixture was stirred for 3.5 hours at 25° C. to 30° C. The reaction mass was filtered through Hyflo® bed and then washed with methanol to obtain a filtrate. The filtrate was taken in a reaction flask and methyl 5-formyl-2-methoxybenzoate (0.15 kg; Formula IVa or IV, when R is methyl)

was added at room temperature. The reaction mixture was stirred for one hour. Methyl 5-formyl-2-methoxybenzoate (15 g; Formula IVa or IV, when R is methyl) was again added at the interval of one hour at room temperature. The pH of the reaction mixture was adjusted to 3.0 to 3.5 using 50% solution of citric acid (~0.7 kg citric acid in 1.4 L water) and then stirred overnight at 10° C. to 25° C. The solid so obtained was filtered, washed with aqueous methanol (50%, 0.3 L) and then suck dried to obtain a wet material. The wet material was washed with water (1.5 L) to obtain a slurry. Methanol (1.2 L) was added to the slurry and then heated to 50° C. to 55° C. The slurry was stirred for 30 minutes at 50° C. to 55° C., cooled to 25° C. to 30° C. and then stirred for one hour. The reaction mixture was filtered, washed with methanol (0.3 L) and then suck dried to obtain a wet cake. The wet cake was dried under vacuum at 50° C. to 55° C. for 20 hours to obtain the title compound.

Yield: 321 g

Chromatographic purity: 99.04%

$^1$H NMR (DMSO, 400 MHz): δ 1.54-1.55 (d, 3H), 2.49-2.66 (m, 4H), 3.78 (s, 3H), 3.82 (s, 3H), 3.90-4.00 (q, 2H), 4.23-4.29 (q, 1H), 7.12-7.27 (m, 1H), 7.12-7.27 (m, 1H), 7.35-7.39 (t, 2H), 7.57-7.61 (dd, 1H), 7.61 (s, 1H), 7.76-7.79 (d, 1H), 7.76-7.79 (d, 2H)

IR $\lambda_{max}$ (KBr): 3423, 3007, 2952, 2842, 2707, 1909, 1702, 1617, 1583, 1502, 1459, 1438, 1389, 1306, 1266, 1208, 1158, 1086, 1121, 1025, 995, 900, 823, 764, 787, 764, 735, 694, 504, 467, 434, 419, 409 cm$^{-1}$.

Mass: 366.2 [M+H]$^+$ of free base

Citrate content (on anhydrous basis (% w/w)): 33.55

Method B:

Benzyl [(1S)-1-(4-phenyl-1H-imidazol-2-yl)ethyl]carbamate (10 g; Formula IIa or Formula II, when PG is benzyloxycarbonyl) was added to methanol (50 mL) at room temperature. Palladium on carbon (2.5%, 1 g) was added to the mixture at room temperature. Hydrogen pressure (3.0 kg/cm$^2$ to 4 kg/cm$^2$) was applied to the reaction mixture and then stirred for 3 hours at 28° C. to 30° C. The reaction mass was filtered through Hyflo® bed and then washed with methanol (20 mL) to obtain a filtrate.

Filtrate was added to a mixture of methanol (70 mL) and molecular sieves (4 Å, 1.0 g). Methyl 5-formyl-2-methoxybenzoate (6.6 g; Formula IVa or IV, when R is methyl) was added to the mixture at room temperature and then stirred for 2 hours. Palladium on carbon (2.5% dry, 1.16 g) was added to the mixture at room temperature. Hydrogen pressure (3.5 kg/cm$^2$) was applied to the reaction mass and then stirred for 6 hours at 30° C. The reaction mixture was filtered through Hyflo® bed and then washed with methanol (20 mL) to obtain a filtrate. An aqueous solution of citric acid (50%, ~23 mL) was added to the reaction mixture at room temperature and then stirred for one hour. The solid so obtained was filtered, washed with water (50 mL), suck dried and then dried overnight in an air oven at 60° C. to 65° C. to obtain the title compound.

Yield: 10 g

Chromatographic purity: 98.26%

Method C:

Benzyl [(1S)-1-(4-phenyl-1H-imidazol-2-yl)ethyl]carbamate (10 g; Formula IIa or Formula II, when PG is benzyloxycarbonyl) was added to methanol (50 mL) at room temperature. Palladium on carbon (2.5%, 50% wet; 4 g) was added at room temperature. Hydrogen pressure (3.0 kg/cm$^2$ to 4.0 kg/cm$^2$) was applied to the reaction mass and then stirred for 2 hours at 30° C. Methyl 5-formyl-2-methoxybenzoate (5.7 g; Formula IVa or IV, when R is methyl) was added to the mixture at room temperature and hydrogen pressure (3.0 kg/cm$^2$ to 4.0 kg/cm$^2$) was applied. The reaction mixture was stirred for 4 hours at 30° C. The reaction mixture was filtered through Hyflo® bed and then washed with methanol (20 mL) to obtain a filtrate. An aqueous solution of citric acid (50%, 14 mL) was added to the filtrate at room temperature to obtain a reaction mass. The reaction mass was stirred for 2 hours at 20° C. to 22° C. The solid so obtained was filtered, washed with water (50 mL), suck dried and then dried overnight in air oven at 60° C. to 65° C. to obtain the title compound.

Yield: 10.3 g

Chromatographic purity: 98.97%

Method D:

Benzyl [(1S)-1-(4-phenyl-1H-imidazol-2-yl)ethyl]carbamate (10 g; Formula IIa or Formula II, when PG is benzyloxycarbonyl) was added to methanol (50 mL) at room temperature. Palladium on carbon (2.5%, 50% wet; 4 g) was added to the mixture at room temperature. Methyl 5-formyl-2-methoxybenzoate (6.3 g; Formula IVa or IV, when R is methyl) was added to the mixture at room temperature and hydrogen pressure (3.5 kg/cm$^2$ to 4.0 kg/cm$^2$) was applied. The reaction mixture was stirred for 2 hours at 30° C. Methyl 5-formyl-2-methoxybenzoate (0.94 g; Formula IVa or IV, when R is methyl) and activated molecular sieves (4 Å, 5 g) were added to the reaction mixture at room temperature. Hydrogen pressure (3.0 kg/cm$^2$ to 4.0 kg/cm$^2$) was again applied to the reaction mixture and then stirred for 4 hours at 30° C. The reaction mixture was filtered through Hyflo® bed and washed with methanol (20 mL) to obtain a filtrate. An aqueous solution of citric acid (50%, 13 mL) was added to the filtrate at room temperature. The reaction mixture was stirred for 2 hours at 20° C. to 22° C. The solid so obtained was filtered, washed with water (50 mL), suck dried and then dried overnight in air oven at 60° C. to 65° C. to obtain the title compound.

Yield: 9.6 g

Chromatographic purity: 95.67%

Example 2: Preparation of methyl 2-methoxy-5-({[(1S)-1-(4-phenyl-1H-imidazol-2-yl)ethyl]amino}methyl)benzoate (Formula VIa or VI, when R is methyl)

Dichloromethane (600 mL), methyl 2-methoxy-5-({[(1S)-1-(4-phenyl-1H-imidazol-2-yl)ethyl]amino}methyl)benzoate citrate (120 g, Formula Va or V when R is methyl, obtained from Example 1) and de-ionized (DI) water (360 mL) were added to a round bottom flask at 18° C. to 19° C. to obtain a reaction mixture. An aqueous solution of sodium hydroxide (20%, 130 mL) was added to the reaction mixture at 18° C. to 22° C. to adjust the pH from 4.0 to 8.0. The reaction mixture was stirred for 10 minutes. The layers were separated and the organic layer was washed with DI water (240 mL). The organic layer was treated with anhydrous sodium sulphate (12 g) and then recovered under vacuum at 40° C. to 45° C. The oil so obtained was dissolved in dichloromethane (750 mL) and recovered under vacuum at 40° C. to 45° C. to obtain an oil.

Example 3: Preparation of methyl 5-({[N-(tert-butoxycarbonyl)-4-carbamoyl-2,6-dimethyl-L-phenylalanyl][(1S)-1-(4-phenyl-1H-imidazol-2-yl)ethyl]amino}methyl)-2-methoxybenzoate The oil (obtained from Example 2) was dissolved in N,N-dimethylformamide (150 mL) to obtain a solution. N-(tert-Butoxycarbonyl)-4-carbamoyl-2,6-dimethyl-L-phenylalanine (50 g; prepared as per procedure disclosed in Example 8 of U.S. Pat. No. 7,741,356) was added to the solution and then stirred for 5 minutes at 25° C. to 27° C. to obtain a clear solution. 1-Ethyl-3-(3-dimethylaminopropyl)carbodiimide (42.74 g) was added and then stirred for 2 hours at 28° C. to 30° C. Dichloromethane (500 mL) and water (400 mL) was added to the solution and then stirred for 10 minutes. The layers were separated and the organic layer was washed with de-ionized water (400 mL) and aqueous sodium bicarbonate solution (2×500 mL). The organic layer was collected and de-ionized water (500 mL) was added. The pH was adjusted to 3.0 using 6N hydrochloric acid (6 mL). The layers were separated and deionized water (500 mL) was added to the organic layer. The pH was adjusted to 2.98 using 6N hydrochloric acid (2 mL). The layers were separated and washed with de-ionized water (500 mL). The organic layer was recovered under vacuum at 40° C. to 45° C. to obtain the title compound.

Yield: 75.06 g
Chromatographic purity: 79.85%

Example 4: Preparation of Eluxadoline of Formula I

Methyl 5-({[N-(tert-butoxycarbonyl)-4-carbamoyl-2,6-dimethyl-L-phenylalanyl][(1S)-1-(4-phenyl-1H-imidazol-2-yl)ethyl]amino}methyl)-2-methoxybenzoate was converted to eluxadoline as per procedure disclosed in U.S. Pat. No. 7,741,356 or as described in our copending application.

Chromatographic purity: 97.56%.

The invention claimed is:
1. A process for the preparation of eluxadoline of Formula I,

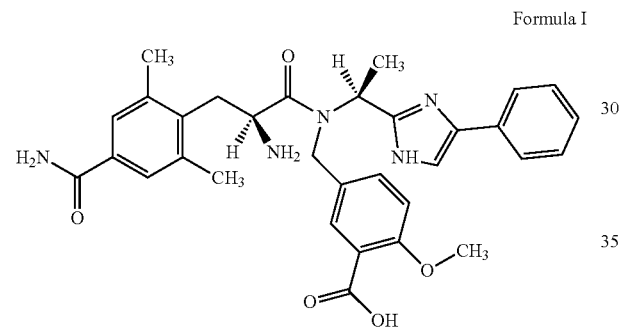

Formula I comprising
a) deprotecting a compound of Formula II

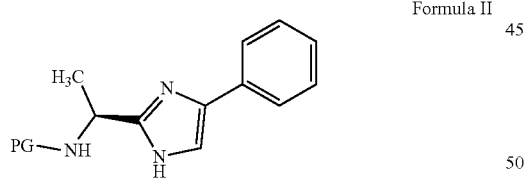

Formula II wherein PG is a nitrogen protecting group;
in the presence of a deprotecting agent to obtain a compound of Formula III;

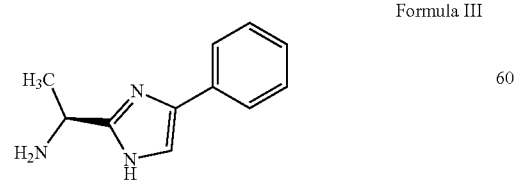

Formula III b) reductive amination of the compound of Formula III with a compound of Formula IV

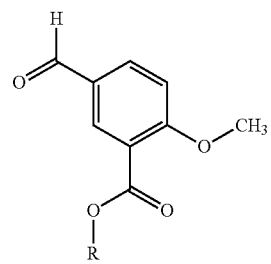

Formula IV wherein R is hydrogen or $C_{1-6}$ alkyl;
followed by the treatment with an acid to obtain a compound of Formula V

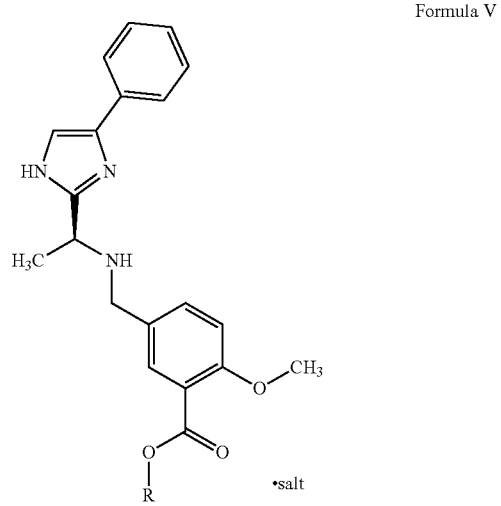

Formula V wherein R is hydrogen or $C_{1-6}$ alkyl; and
c) converting the compound of Formula V to eluxadoline of Formula I.

2. A compound of Formula V,

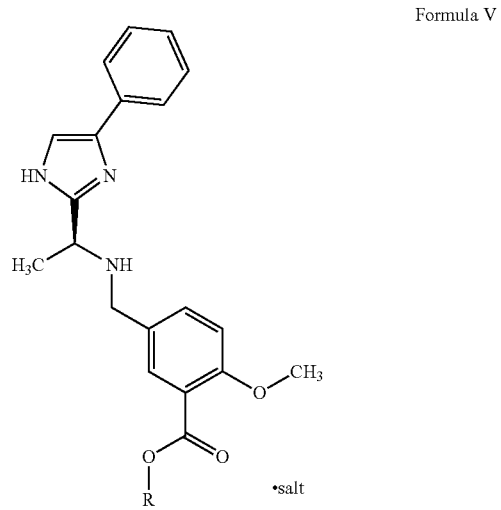

Formula V wherein the salt is selected from the group consisting of citrate, acetate, fumarate, lactate, maleate, malate, tartrate, benzoate, mesylate, oxalate, tosylate, and succinate; and
wherein R is hydrogen or $C_{1-6}$ alkyl.

3. A compound of Formula Va,

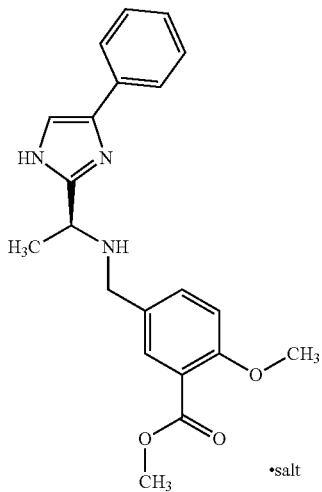

Formula Va

•salt wherein the salt is selected from the group consisting of citrate, acetate, fumarate, lactate, maleate, malate, tartrate, benzoate, mesylate, oxalate, tosylate, and succinate.

4. The process according to claim 1, wherein the acid is selected from the group consisting of citric acid, acetic acid, fumaric acid, lactic acid, maleic acid, malic acid, tartaric acid, benzoic acid, methanesulfonic acid, oxalic acid, p-toluenesulfonic acid, and succinic acid.

5. The process according to claim 1, wherein the reductive amination is carried out in the presence of a reducing agent in a solvent.

6. The process according to claim 5, wherein the reducing agent is selected from the group consisting of sodium borohydride, sodium cyanoborohydride, sodium triacetoxyborohydride, lithium borohydride, potassium borohydride, Raney Nickel, and Palladium on carbon (Pd/C).

7. The process according to claim 4, wherein the solvent is selected from the group consisting of alcohols, nitriles, halogenated hydrocarbons, ethers, water, and mixtures thereof.

8. The process according to claim 1, wherein the compound of Formula V is converted into Eluxadoline of Formula I by treating the compound of Formula V with a base in a solvent to obtain a compound of Formula VI,

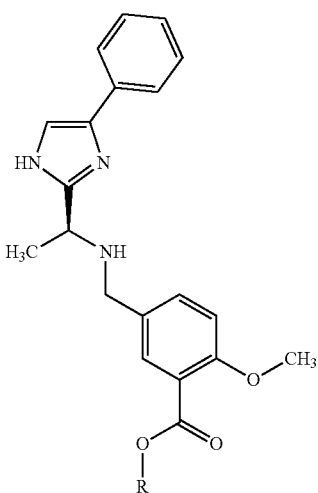

Formula VI wherein R is hydrogen or $C_{1-6}$ alkyl; and
converting the compound of Formula VI into Eluxadoline of Formula I.

9. The process according to claim 7, wherein the base is selected from the group consisting of sodium hydroxide, potassium hydroxide, lithium hydroxide, calcium hydroxide, sodium bicarbonate, potassium bicarbonate, and cesium hydroxide.

10. The process according to claim 7, wherein the solvent is selected from the group consisting of alcohols, nitriles, halogenated hydrocarbons, ethers, water, and mixtures thereof.

* * * * *